(12) United States Patent
Ni et al.

(10) Patent No.: US 7,840,267 B2
(45) Date of Patent: Nov. 23, 2010

(54) CLOSED-LOOP RESYNCHRONIZATION THERAPY FOR MECHANICAL DYSSYNCHRONY

(75) Inventors: Quan Ni, Shoreview, MN (US); Christopher Hartemink, Shoreview, MN (US); Andres Belalcazar, St. Paul, MN (US); Allan C. Shuros, St. Paul, MN (US); Loell Boyce Moon, Ham Lake, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 796 days.

(21) Appl. No.: 11/690,700

(22) Filed: Mar. 23, 2007

(65) Prior Publication Data
US 2008/0234773 A1  Sep. 25, 2008

(51) Int. Cl.
*A61N 1/368* (2006.01)
(52) U.S. Cl. .............................. 607/9; 600/547; 607/18; 607/62
(58) Field of Classification Search ........................ None
See application file for complete search history.

(56) References Cited

U.S. PATENT DOCUMENTS

| | | | |
|---|---|---|---|
| 4,202,340 A | 5/1980 | Langer et al. | |
| 5,058,583 A * | 10/1991 | Geddes et al. | 607/6 |
| 5,179,946 A | 1/1993 | Weiss | |
| 5,385,576 A | 1/1995 | Noren et al. | |

(Continued)

FOREIGN PATENT DOCUMENTS

WO   WO-2008/118349 A1   10/2008

OTHER PUBLICATIONS

Belalcazar, Andres, "Method and Apparatus for Detecting Fibrillation Using Cardiac Local Impedance", U.S. Appl. No. 11/550,923, filed Oct. 19, 2006, 38 Pages.

(Continued)

*Primary Examiner*—Kennedy J Schaetzle
(74) *Attorney, Agent, or Firm*—Schwegman, Lundberg & Woessner, P.A.

(57) ABSTRACT

An apparatus comprises a first impedance sensing circuit, a second sensing circuit, and an impedance-based cardiac dyssynchrony detector. The impedance sensing circuit senses an intracardiac local impedance signal that is indicative of a cardiac local wall motion of a first cardiac region from an implantable first bipolar pair of impedance sensing electrodes. The second sensing circuit is configured to produce a second sensor signal indicative of cardiovascular activity. The impedance-based cardiac dyssynchrony detector is configured for detecting cardiac dyssynchrony using a relationship between the first intracardiac local impedance signal and the second sensor signal. Other apparatuses and methods are disclosed.

37 Claims, 9 Drawing Sheets

U.S. PATENT DOCUMENTS

| | | | |
|---|---|---|---|
| 6,070,100 | A | 5/2000 | Bakels et al. |
| 6,076,015 | A | 6/2000 | Hartley et al. |
| 6,219,579 | B1 | 4/2001 | Bakels et al. |
| 6,223,079 | B1 | 4/2001 | Bakels et al. |
| 6,223,082 | B1 | 4/2001 | Bakels et al. |
| 6,238,420 | B1 | 5/2001 | Bakels et al. |
| 6,278,894 | B1 | 8/2001 | Salo et al. |
| 6,754,530 | B2 | 6/2004 | Bakels et al. |
| 6,871,088 | B2 | 3/2005 | Chinchoy |
| 6,885,889 | B2 | 4/2005 | Chinchoy |
| 7,190,996 | B2 * | 3/2007 | Jarverud ............... 600/547 |
| 7,203,541 | B2 * | 4/2007 | Sowelam et al. ......... 607/19 |
| 7,440,803 | B2 | 10/2008 | Ni et al. |
| 7,640,058 | B2 * | 12/2009 | Lang ..................... 607/17 |
| 2001/0010009 | A1 | 7/2001 | Bakels et al. |
| 2002/0002389 | A1 | 1/2002 | Bradley et al. |
| 2002/0143368 | A1 | 10/2002 | Bakels et al. |
| 2003/0199955 | A1 | 10/2003 | Struble et al. |
| 2005/0038481 | A1 | 2/2005 | Chinchoy et al. |
| 2005/0154421 | A1 | 7/2005 | Ousdigian |
| 2006/0271119 | A1 | 11/2006 | Ni et al. |
| 2006/0271121 | A1 | 11/2006 | Ding et al. |
| 2006/0293714 | A1 * | 12/2006 | Salo et al. ............... 607/9 |
| 2007/0005114 | A1 | 1/2007 | Salo et al. |
| 2007/0066905 | A1 | 3/2007 | Zhang |
| 2008/0097539 | A1 | 4/2008 | Belalcazar |

OTHER PUBLICATIONS

Griesbach, L., et al., "Clinical performance of automatic closed-loop stimulation systems.", *Pacing Clin Electrophysiol.*, 26(7 Pt 1), (Jul. 2003), 1432-7.

"International Application Serial No. PCT/US2008/003720, International Search Report mailed Aug. 19, 2008", 4 pgs.

"International Application Serial No. PCT/US2008/003720, Written Opinion mailed Aug. 19, 2008", 6 pgs.

"U.S. Appl. No. 11/550,923, Non-Final Office Action mailed Jul. 17, 2009", 11 pgs.

"U.S. Appl. No. 11/550,923, Response filed Jun. 4, 2009 to Restriction Requirement mailed May 7, 2009", 7 pgs.

"U.S. Appl. No. 11/550,923, Response filed Oct. 19, 2009 to Non Final Office Action mailed Jul. 17, 2009", 13 pgs.

"U.S. Appl. No. 11/550,923, Restriction Requirement mailed May 7, 2009", 6 pgs.

"U.S. Appl. No. 11/550,923, Final Office Action mailed Feb. 5, 2010", 16 pgs.

* cited by examiner

CLOSED-LOOP RESYNCHRONIZATION THERAPY FOR MECHANICAL DYSSYNCHRONY

FIELD OF THE INVENTION

The field generally relates to implantable medical devices and, in particular, but not by way of limitation, to monitoring cardiac impedance of a subject to enhance detection of heart chamber mechanical dyssynchrony.

BACKGROUND

Implantable medical devices (IMDs) are devices designed to be implanted into a patient. Some examples of these devices include cardiac function management (CFM) devices such as implantable pacemakers, implantable cardioverter defibrillators (ICDs), cardiac resynchronization devices, and devices that include a combination of such capabilities. The devices are typically used to treat patients using electrical or other therapy or to aid a physician or caregiver in patient diagnosis through internal monitoring of a patient's condition. The devices may include one or more electrodes in communication with one or more sense amplifiers to monitor electrical heart activity within a patient, and often include one or more sensors to monitor one or more other internal patient parameters. Other examples of implantable medical devices include implantable diagnostic devices, implantable drug delivery systems, or implantable devices with neural stimulation capability.

Additionally, some IMDs detect events by monitoring one or more electrical heart activity signals. In CFM devices, these events include heart chamber expansions or contractions. By monitoring cardiac signals indicative of expansions or contractions, IMDs are able to detect heart chamber mechanical dyssynchrony, such as when the right ventricle and the left ventricle are not contracting in unison. Cardiac resynchronization therapy (CRT) may be provided to correct the cardiac dyssynchrony. Typically, IMDs that detect cardiac dyssynchrony look to cardiac events that are global to contractions of the heart, such as estimating heart chamber volumes for example. However, cardiac dyssynchrony may be difficult to define and determine.

SUMMARY

This document relates generally to devices and methods for assessing the cardiac dyssynchrony of a patient as indicated through intracardiac local impedance. A device example includes a first impedance sensing circuit, a second sensing circuit and an impedance-based cardiac dyssynchrony detector. The impedance sensing circuit senses an intracardiac local impedance signal that is indicative of a cardiac local wall motion of a first cardiac region from an implantable first bipolar pair of impedance sensing electrodes. The second sensing circuit is configured to produce a second sensor signal indicative of cardiovascular activity. The impedance-based cardiac dyssynchrony detector is configured for detecting cardiac dyssynchrony using a relationship between the first intracardiac local impedance signal and the second sensor signal.

A method example includes sensing an intracardiac local impedance signal indicative of a cardiac local wall motion using an implantable medical device (IMD), sensing at least a second sensor signal indicative of cardiovascular activity, and detecting cardiac dyssynchrony using a relationship between the intracardiac local impedance signal and the second sensor signal.

This summary is intended to provide an overview of the subject matter of the present patent application. It is not intended to provide an exclusive or exhaustive explanation of the invention. The detailed description is included to provide further information about the subject matter of the present patent application.

DETAILED DESCRIPTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a nonexclusive or, such that "A or B" includes "A but not B," "B but not A," and "A and B," unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

Figure 1:
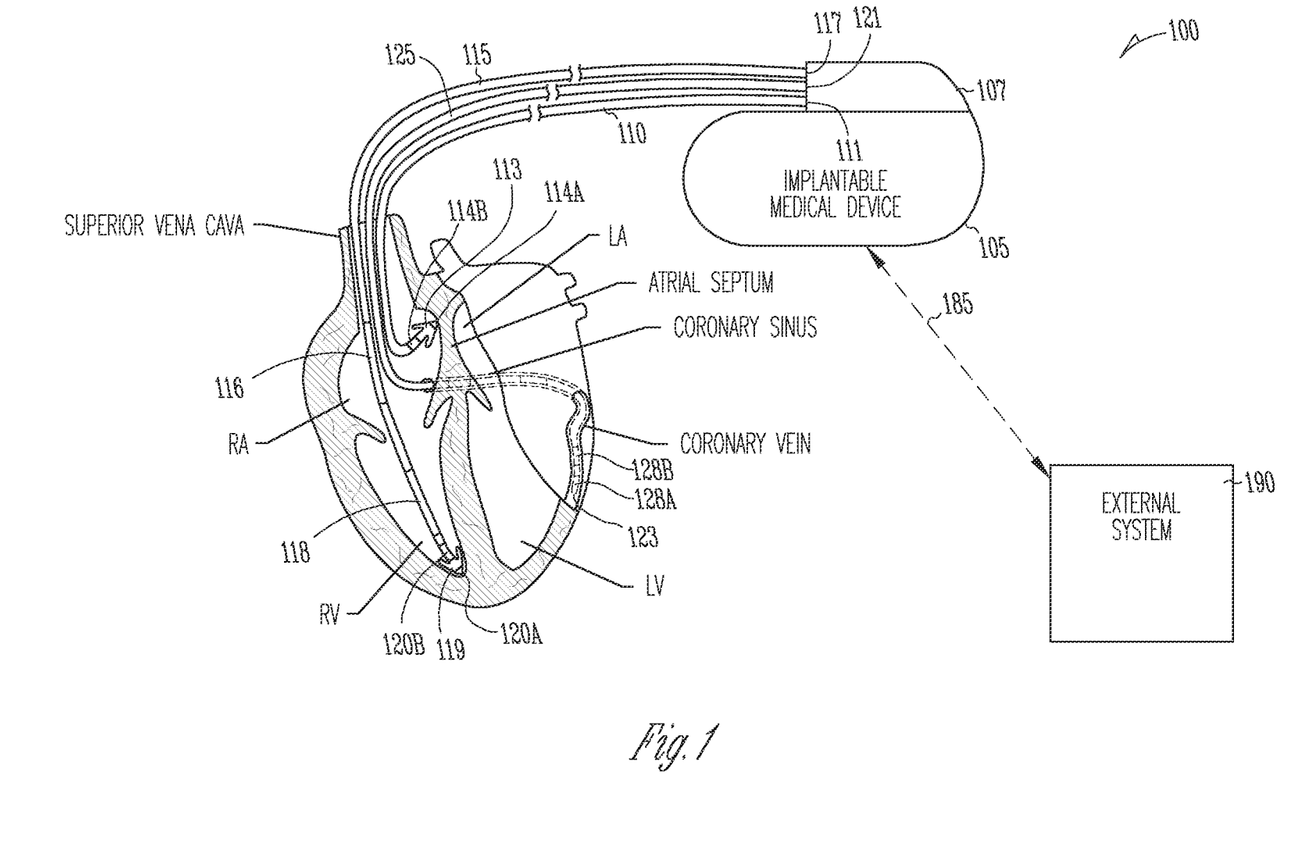
FIG. 1 is a block diagram of portions of a system that uses an IMD.

FIG. 1 is an illustration of portions of a system 100 that uses an implantable medical device (IMD) 105. Examples of IMD 105 include, without limitation, a, pacemaker, a cardioverter, a defibrillator, a cardiac resynchronization therapy (CRT) device, and other cardiac monitoring and therapy delivery devices, including cardiac devices that include or work in coordination with one or more neuro-stimulating devices, drugs, drug delivery systems, or other therapies. As one example, the system 100 shown is used to treat a cardiac arrhythmia. The IMD 105 typically includes an electronics unit coupled by one or more cardiac leads 110, 115, 125, to a heart of a patient or subject. The electronics unit of the IMD 105 typically includes components that are enclosed in a hermetically-sealed canister or "can." System 100 also typically includes an IMD programmer or other external system 190 that communicates one or more wireless signals 185 with the IMD 105, such as by using radio frequency (RF) or one or more other telemetry signals.

The example shown includes right atrial (RA) lead 110 having a proximal end 111 and a distal end 113. Proximal end 111 is coupled to a header connector 107 of the IMD 105. Distal end 113 is configured for placement in the RA in or near the atrial septum. RA lead 110 may include a pair of bipolar electrodes, such as an RA tip electrode 114A and an RA ring electrode 114B. RA electrodes 114A and 114B are incorporated into the lead body at distal end 113 for placement in or near the atrial septum, and are each electrically coupled to IMD 105 through a conductor extending within the lead body. In some embodiments, RA electrodes 114A and 114B function as a pair of RA impedance sensing electrodes for sensing an RA local impedance signal. The distance between RA tip electrode 114A and RA ring electrode 114B is in a range of approximately 2 millimeters to 20 millimeters, with approximately 5 millimeters being a specific example.

The example shown also includes right ventricular (RV) lead 115 having a proximal end 117 and a distal end 119. Proximal end 117 is coupled to header connector 107. Distal end 119 is configured for placement in the RV. RV lead 115 may include one or more of a proximal defibrillation electrode 116, a distal defibrillation electrode 118, an RV tip electrode 120A, and an RV ring electrode 120B. Defibrillation electrode 116 is incorporated into the lead body in a location suitable for supraventricular placement in the RA and/or the superior vena cava. Defibrillation electrode 118 is incorporated into the lead body near distal end 119 for placement in the RV. RV electrodes 120A and 120B may form a bipolar electrode pair and are incorporated into the lead body at distal end 119. Electrodes 116, 118, 120A, and 120B are each electrically coupled to IMD 105 through a conductor extending within the lead body. Proximal defibrillation electrode 116, distal defibrillation electrode 118, and/or an electrode formed on the can of IMD 105 allow for delivery of cardioversion/defibrillation pulses to the heart.

RV tip electrode 120A, RV ring electrode 120B, and/or an electrode formed on the can of IMD 105 allow for sensing an RV electrogram indicative of RV depolarizations and delivering RV pacing pulses. Sensing and pacing allows the IMD 105 to adjust timing of the heart chamber contractions. For example, IMD 105 can adjust the timing of ventricular contractions with respect to the timing of atrial contractions delay by sensing a contraction in the RA and pacing the RV at the desired atrial-ventricular (AV) delay time. In one embodiment, RV electrodes 120A and 120B function as a pair of RV impedance sensing electrodes for sensing an RV local impedance signal. The distance between RV tip electrode 120A and RV ring electrode 120B is in a range of approximately 2 millimeters to 20 millimeters, with approximately 8 millimeters being a specific example. In some examples, RV ring electrode 120B may form a bipolar electrode pair with defibrillation electrode 118. RV ring electrode 120B and defibrillation electrode 118 may function as a pair of RV impedance sensing electrodes for sensing an RV impedance signal.

Also shown is a left ventricular (LV) lead 125. LV lead 125 is a coronary pacing and/or sensing lead that includes an elongate lead body having a proximal end 121 and a distal end 123. Proximal end 121 is coupled to header connector 107. Distal end 123 is configured for placement or insertion in the coronary vein. LV lead 125 may include an LV tip electrode 128A and an LV ring electrode 128B. The distal portion of lead 125 is configured for placement in the coronary sinus and coronary vein such that LV electrodes 128A and 128B are placed in the coronary vein. LV electrodes 128A and 128B may form a bipolar electrode pair and are incorporated into the lead body at distal end 123 and each electrically coupled to IMD 105 through a conductor extending within the lead body. LV tip electrode 128A, LV ring electrode 128B, and/or an electrode formed on the can of IMD 105 allow for sensing an LV electrogram indicative of LV depolarizations and delivering LV pacing pulses. In one example, LV electrodes 128A and 128B function as a pair of LV impedance sensing electrodes for sensing an LV local impedance signal. The distance between LV tip electrode 128A and LV ring electrode 128B is in a range of approximately 2 millimeters to 40 millimeters, with approximately 11 millimeters being a specific example.

Figure 2:
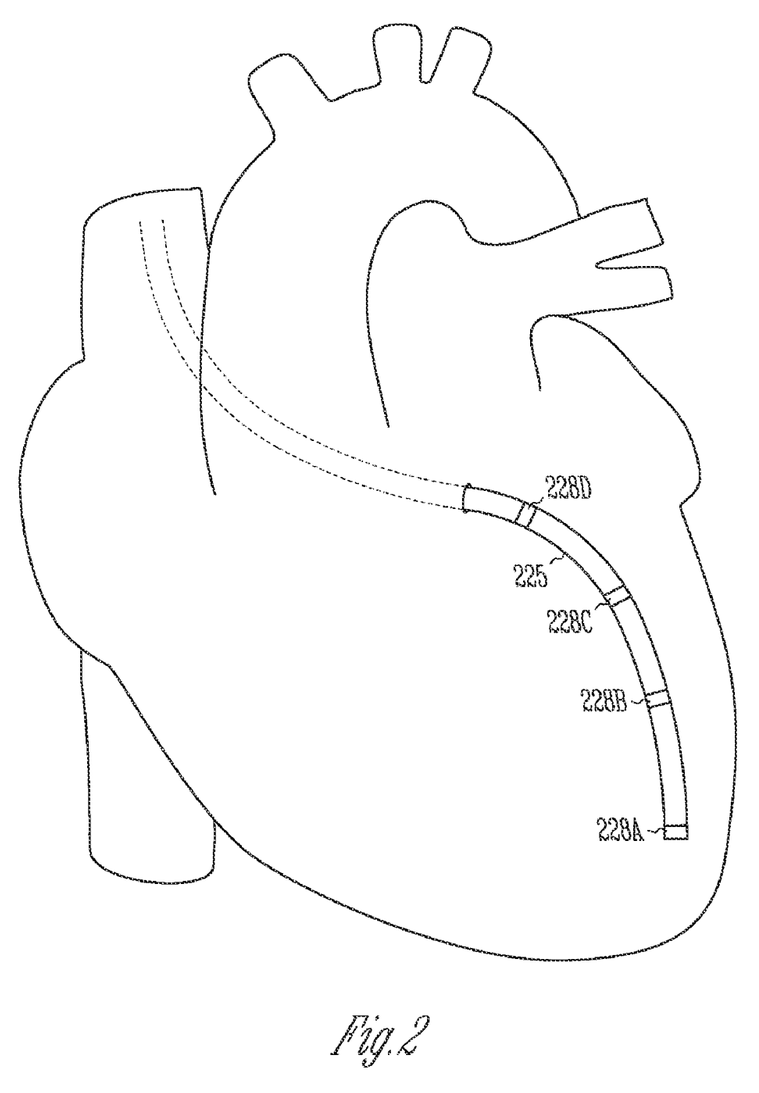
FIG. 2 is an illustration of a portion of a left ventricular lead 225 that includes multiple electrodes.

In some examples, LV lead 125 includes additional electrodes. FIG. 2 is an illustration of a portion of a LV lead 225 that includes LV electrodes 228A, 228B, 228C, and 228D. LV electrode 228A may be a tip or ring electrode and LV electrodes 228B, 228C, and 228D are ring electrodes. In one example, LV electrodes 228B and 228C function as a pair of LV impedance sensing electrodes for sensing an LV local impedance signal. In another example, LV electrodes 228C and 228D function as a pair of LV impedance sensing electrodes for sensing an LV local impedance signal.

Other forms of electrodes include meshes and patches, which may be applied to one or more portions of heart, or which may be implanted in one or more other areas of the body to help "steer" electrical current produced by IMD 105 in FIG. 1. The IMDs may be configured with a variety of electrode arrangements, including transvenous, endocardial, or epicardial electrodes (e.g., intrathoracic electrodes), or subcutaneous, non-intrathoracic electrodes, such as can, header, or indifferent electrodes, or subcutaneous array or lead electrodes (e.g., non-intrathoracic electrodes). Monitoring of electrical signals related to cardiac activity may provide early, if not immediate, diagnosis of cardiac disease.

Figure 3:
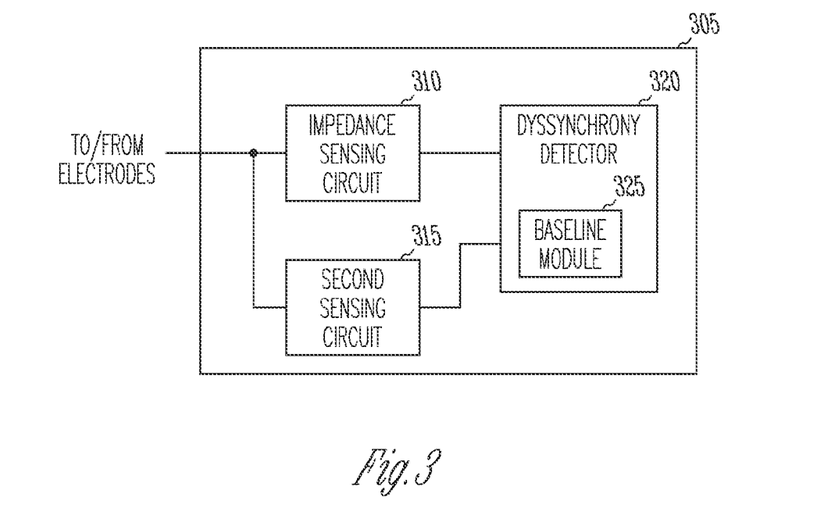
FIG. 3 shows a block diagram of portions of an example of a device for monitoring cardiac impedance of a subject.

FIG. 3 shows a block diagram of portions of an example of a device 305 for monitoring cardiac impedance of a subject. In some examples, the portions are included in an IMD. The device 305 includes an impedance sensing circuit 310 and a second sensing circuit 315. The impedance sensing circuit 310 senses an intracardiac impedance local impedance signal from an implantable first bipolar pair of impedance sensing electrodes. The impedance sensing circuit 310 injects a known current and senses the voltage signal resulting from the current. The voltage signal is divided by the current to form an intracardiac local impedance signal. The intracardiac local impedance signal is indicative of a cardiac local wall motion of a cardiac region.

Figure 4:
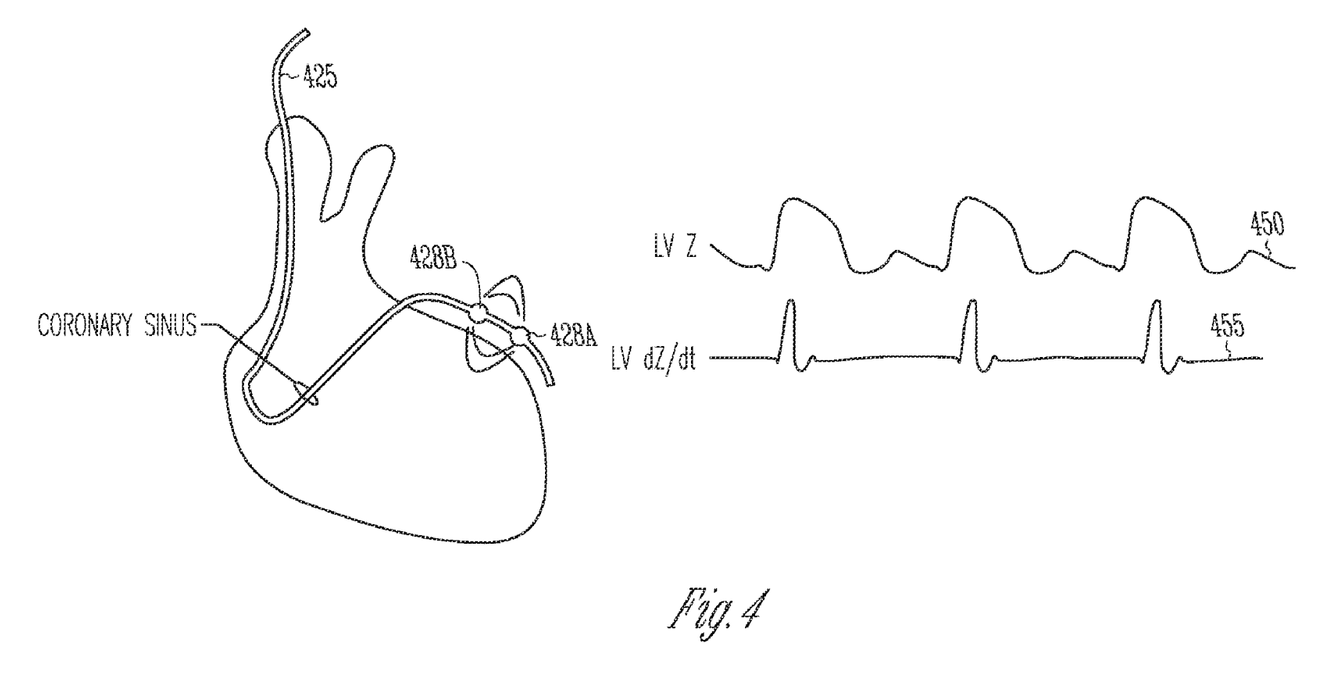
FIG. 4 shows an illustration of an example of sensing an intracardiac local impedance signal using implantable electrodes.

FIG. 4 shows an illustration of an example of sensing such a local impedance signal using implantable electrodes. In the example, the impedance sensing electrodes 428A and 428B are included in a cardiac lead 425 shaped and sized for inserting into a coronary sinus and for placement on the left ventricle (LV) free wall. The impedance sensing electrodes 428A, 428B are communicatively coupled to the impedance sensing circuit 310. The impedance sensing electrodes 428A, 428B are configured as a bipolar electrode pair. The impedance sensing circuit 310 uses the impedance sensing electrodes 428A, 428B to inject a current and sense the resulting voltage indicative of the LV intracardiac local impedance. The sensed intracardiac local impedance signal is indicative of LV local wall motion and/or geometrical changes of the myocardial region in the vicinity of the impedance sensing electrodes 428A, 428B.

FIG. 4 also illustrates an example of a sensed intracardiac local impedance signal 450. The intracardiac local impedance signal 450 represents an impedance signal sensed using impedance sensing electrodes 428A, 428B. The variations in the intracardiac local impedance signal 450 represent LV local wall motion during the systolic phase of cardiac cycles. FIG. 4 further shows an illustration of an example of a rate of change of intracardiac impedance signal 455 derived from the sensed intracardiac local impedance signal 450. The variations in the rate of change signal 455 of the intracardiac local impedance signal represent the rate of change of local wall motion during the systolic phase of cardiac cycles. This rate of change of motion can be viewed as the velocity of the cardiac wall. In some examples, the device 305 includes a differentiator coupled to the impedance sensing circuit 310 to calculate the rate of change as dZ/dt of a sensed intracardiac local impedance signal Z(t). In some examples, the differentiator calculates the rate of change as an estimate of dZ/dt using a measure of $\Delta Z/\Delta t$, such as $$\frac{\Delta Z}{\Delta t} = \frac{Z_2 - Z_1}{t_2 - t_1}, \quad (1)$$

where $Z_1$ and $Z_2$ are values of an intracardiac local impedance signal Z(t) sampled at times $t_1$ and $t_2$ respectively.

An intracardiac local impedance signal is sensed by bipolar electrodes, such as bipolar electrodes on a pacing or defibrillation lead. The intracardiac local impedance signal is therefore a measure of impedance for a local cardiac region. The size of the local region is determined from the spacing of the bipolar electrodes. In some examples, the distance between the two impedance sensing electrodes may be within a range of approximately 2 millimeters to 40 millimeters. In some examples, the distance between the two impedance sensing electrodes may be within approximately 20 millimeters. This is contrast to measuring heart chamber volume impedances. In chamber volume measurements, a measure of change in impedance for a heart chamber as a whole is used to estimate volume changes due to filling an emptying of blood in the chamber. These chamber volume measurements may be difficult to measure due to the nature of typical implantable cardiac electrodes. In measuring intracardiac local impedance, myocardial wall motion is estimated at the region of the impedance sensing electrodes 428A and 428B.

Returning to FIG. 3, the second sensing circuit 315 produces a second sensor signal. The second sensor signal is indicative of cardiovascular activity. The device 305 also includes an impedance-based cardiac dyssynchrony detector 320. The cardiac dyssynchrony detector 320 detects cardiac dyssynchrony using a relationship between the first intracardiac local impedance signal and the second sensor signal. In some examples, the cardiac dyssynchrony detector 320 detects cardiac dyssynchrony using a relationship between the rate of change of the first intracardiac local impedance signal and the second sensor signal.

In some examples, the second sensing circuit 315 includes a second impedance sensing circuit to sense a second intracardiac local impedance signal from a second bipolar pair of impedance sensing electrodes placed in a different cardiac region than the first bipolar pair of electrodes. It may be preferable for the second bipolar pair to be placed in or on a different cardiac wall than the first pair. In this way, the second sensor signal is indicative of cardiac local wall motion of a different cardiac wall. The cardiac dyssynchrony detector 320 detects cardiac dyssynchrony using a relationship between the first intracardiac local impedance signal obtained from the first cardiac region and the second intracardiac local impedance signal obtained from the second cardiac region.

Figure 5:
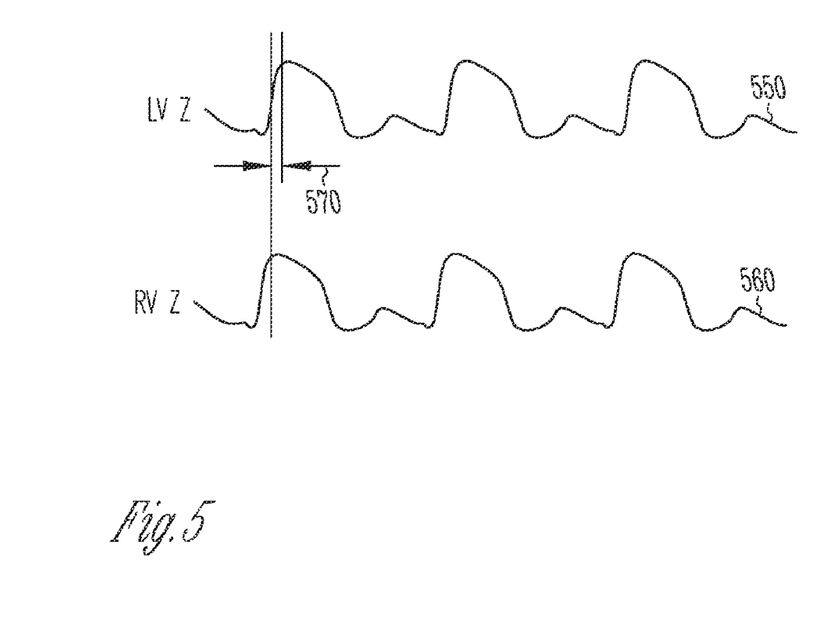
FIG. 5 is an illustration of an example of sensing intracardiac local impedance signals using implantable electrodes placed in two cardiac regions.

FIG. 5 is an illustration of an example of sensing intracardiac local impedance signals using implantable electrodes placed in two cardiac regions. In the example, impedance sensing electrodes 528A and 528B are included in a cardiac lead 525 configured by shape and size for insertion into a coronary sinus and for placement on the LV free wall. Impedance sensing electrodes 520A and 520B are configured as a bipolar electrode pair and are included in a cardiac lead 515 configured by shape and size for placement on a right ventricle (RV) apex, or apical region. Impedance sensing electrodes 520A and 520B are part of a second impedance sensing circuit and sense an intracardiac local impedance signal from the RV free wall. The cardiac dyssynchrony detector 320 detects cardiac dyssynchrony using the temporal relationship between the first intracardiac local impedance signal from the LV free wall and the second intracardiac local impedance signal from the RV apex. When the LV and RV contract in unison, the heart contraction indications of the local impedance signals from the LV and RV occur approximately simultaneously during each cardiac cycle or within a limited interventricular delay.

FIG. 5 illustrates a LV intracardiac local impedance signal 550 and a RV intracardiac local impedance signal 560. The variations in the intracardiac local impedance signals 550, 560 represent RV and LV local wall motion during the systolic phase of cardiac cycles. When the LV and RV do not contract in unison, the heart contraction indications will differ by a time interval or by a time interval that exceeds an interventricular delay threshold value. In some examples, the cardiac dyssynchrony detector 320 detects cardiac dyssynchrony using a time difference between the systolic phases indicated by the local impedance signals of the RV and LV. In some examples, the cardiac dyssynchrony detector 320 detects cardiac dyssynchrony when a time interval 570 between the indicated systolic phase of the RV and the LV exceeds a specified time difference value threshold.

In some examples, the cardiac dyssynchrony detector 320 uses a correlation between the two local impedance signals to detect dyssynchrony, such as a correlation analysis. In some examples, the correlation analysis includes calculating a correlation coefficient between the two local impedance signals. A point-to-point morphology comparison is made by the cardiac dyssynchrony detector 320 between the two sensed local impedance signals. The comparison is given a score sometimes called a feature correlation coefficient (FCC). If the FCC is less than a threshold FCC value, then the two local impedance signals are deemed to be dyssynchronous.

Figure 6:
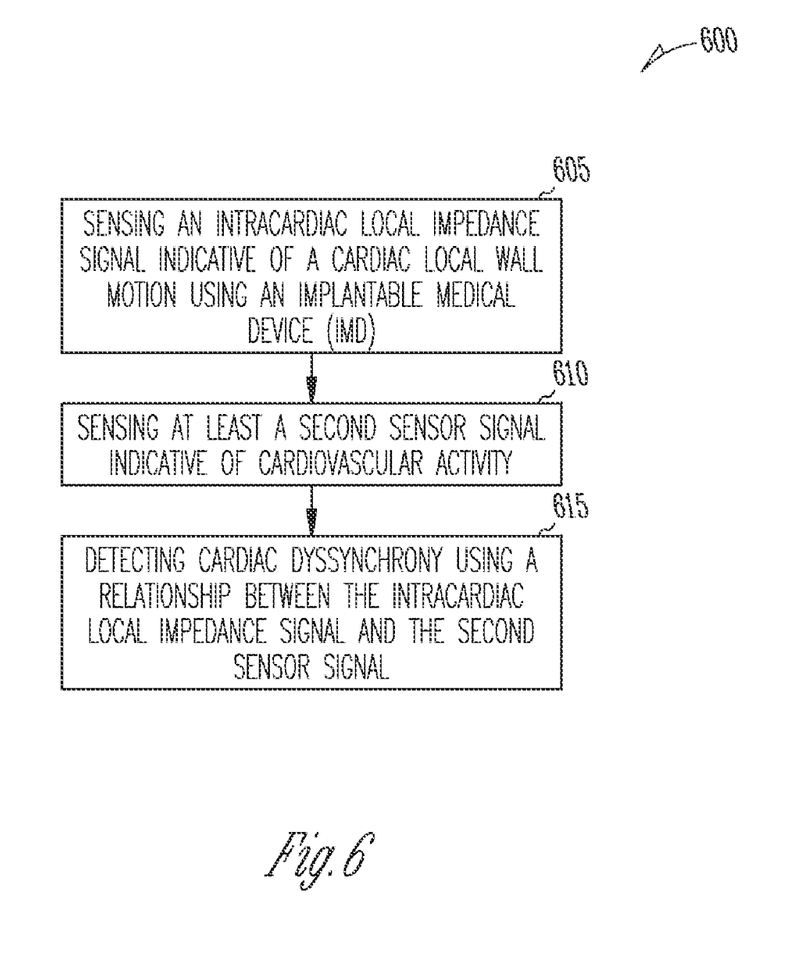
FIG. 6 is a flow diagram of a method of monitoring cardiac impedance of a subject.

FIG. 6 is a flow diagram of a method 600 of monitoring cardiac impedance of a subject. At block 605, an intracardiac local impedance signal is sensed using a device such as the device 305 in FIG. 3. The intracardiac local impedance signal is indicative of a cardiac local wall motion. At block 610, a second sensor signal is sensed. The second sensor signal is indicative of cardiovascular activity. In some examples, the second sensor signal is a second intracardiac local impedance signal. At block 615, cardiac dyssynchrony is detected using a relationship between the intracardiac local impedance signal and the second sensor signal. In some examples, the relationship includes a temporal relationship. In some examples, cardiac dyssynchrony is detected using a correlation analysis of the intracardiac local impedance signal and the second sensor signal.

Returning to FIG. 3, in some examples, the cardiac dyssynchrony detector 320 of FIG. 3 includes a baseline module 325. The baseline module 325 establishes a baseline time interval between the LV intracardiac local impedance signal 550 of FIG. 5 and the RV intracardiac local impedance signal 560. The cardiac dyssynchrony detector 320 detects cardiac dyssynchrony when a measured time interval 570 between the intracardiac local impedance signals 550, 560 changes from the baseline time interval by a specified amount.

In certain examples, the baseline module 325 establishes a baseline correlation coefficient. The cardiac dyssynchrony detector 320 detects cardiac dyssynchrony when a measured correlation coefficient differs from the baseline correlation coefficient by a specified threshold value.

Other arrangements of impedance sensing electrodes may be used to compare intracardiac local impedance signals from other cardiac regions. For example, intracardiac local impedance measurements from a RV free wall may be used. In another example, an intracardiac impedance measurement from a ventricle septal wall may be used.

Figure 7:
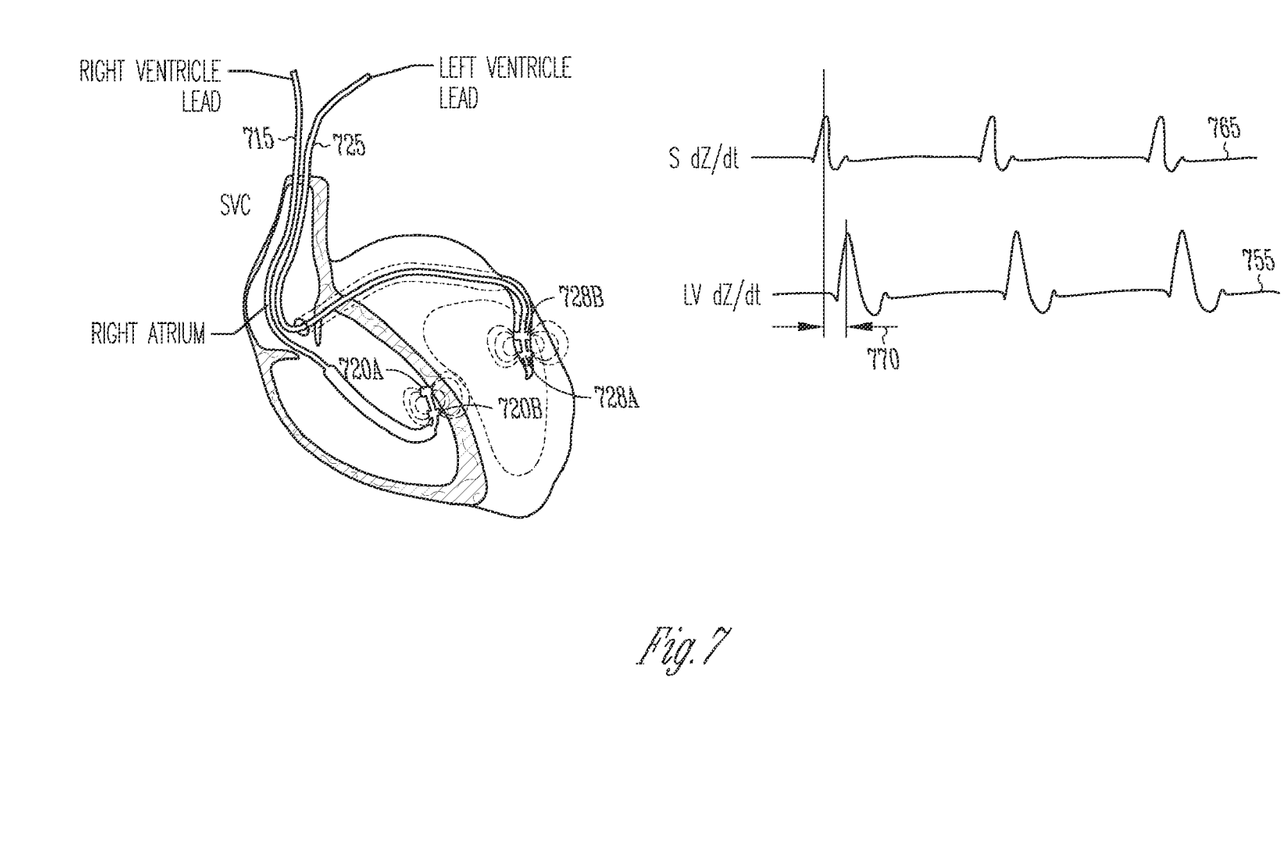
FIG. 7 is another illustration of an example of sensing intracardiac local impedance signals using implantable electrodes placed in two cardiac regions.

FIG. 7 is another illustration of an example of sensing intracardiac local impedance signals using implantable electrodes placed in two cardiac regions. In the example, impedance sensing electrodes 728A and 728B are included in a cardiac lead 725 configured by shape and size for insertion into a coronary sinus and for placement on the LV free wall. Impedance sensing electrodes 720A and 720B are configured as a bipolar electrode pair and are included in a cardiac lead 715 that is configured by shape and size for placement on a RV septal wall. The electrodes are communicatively coupled to the impedance sensing circuit and sense intracardiac local impedance signals from the LV free wall and the RV septal wall. A differentiator may obtain the rate of change in intracardiac impedance from the signals.

FIG. 7 illustrates a LV intracardiac local impedance rate of change signal 755 and a RV intracardiac local impedance rate of change signal 765. The variations in the intracardiac local impedance rate of change signals 755, 765 are indicative of a rate of change of local wall motion of the RV and LV during the systolic phase of cardiac cycles. In some examples, the cardiac dyssynchrony detector 320 detects cardiac dyssynchrony from a time difference between the indicated systolic phases of the local impedance rate of change signals of the RV and LV. In some examples, the cardiac dyssynchrony detector 320 detects cardiac dyssynchrony when a time interval 770 between indicated heart chamber contractions of the RV local impedance signal and the LV local impedance signal exceeds a specified time interval value threshold. The cardiac dyssynchrony detector 320 may use a readily identifiable feature in the rate of change signals that indicates a systolic phase to establish a time interval 770. In some examples, the cardiac dyssynchrony detector uses a peak of the rate of change signals to determine the time interval between the systolic phases of the signals.

In some examples, the cardiac dyssynchrony detector 320 includes a baseline module 325 and establishes a baseline time interval between the rate of change signals. The cardiac dyssynchrony detector 320 detects dyssynchrony when a measured time interval 770 changes from the baseline interval by a specified threshold time interval value. In some examples, the cardiac dyssynchrony detector 320 determines a correlation coefficient among the rate of change signals and detects dyssynchrony when the correlation coefficient is less than a specified value. In some examples, a baseline correlation coefficient is established and cardiac dyssynchrony is detected when a measured correlation coefficient changes from the baseline correlation coefficient by a specified threshold value.

Figure 8:
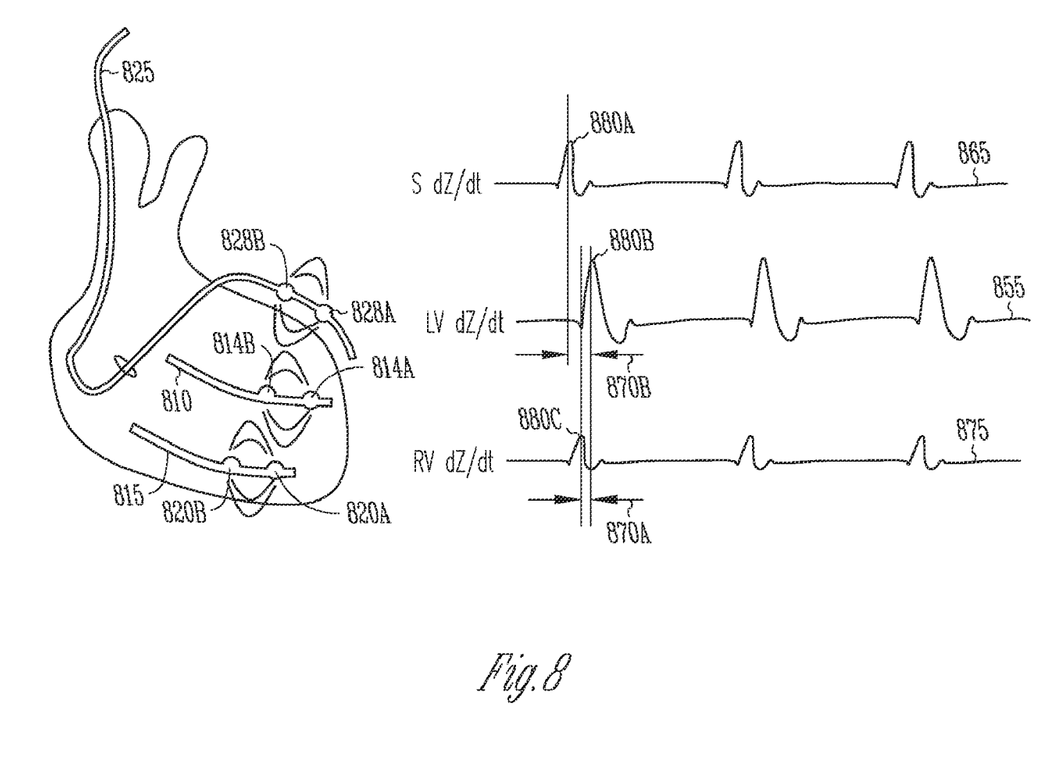
FIG. 8 is an illustration of an example of sensing intracardiac local impedance signals using implantable electrodes placed in three cardiac regions.

FIG. 8 is an illustration of an example of sensing intracardiac local impedance signals using implantable electrodes placed in three cardiac regions. In the example, impedance sensing electrodes 828A and 828B are included in a cardiac lead 825 configured by shape and size for insertion into a coronary sinus and for placement on the LV free wall. Impedance sensing electrodes 820A and 820B are configured as a bipolar electrode pair and are included in a cardiac lead 815 that is configured for placement on a RV apex. Impedance sensing electrodes 814A and 814B are configured as a bipolar electrode pair and are included in a cardiac lead 810 that is configured for placement on a RV septal wall. Electrodes 814A and 814B are part of a third impedance sensing circuit and sense intracardiac local impedance signals from the RV septal wall. The cardiac dyssynchrony detector 320 of FIG. 3 may detect cardiac dyssynchrony using intracardiac local impedance signals obtained from the impedance sensing electrodes.

In some examples, the cardiac dyssynchrony detector 320 uses the rate of change of the sensed intracardiac local impedance signals to detect cardiac dyssynchrony. The cardiac dyssynchrony detector 320 may also use a relationship of heart chamber contractions indications included in the three sensed intracardiac local impedance signals to detect cardiac dyssynchrony.

FIG. 8 illustrates a LV intracardiac local impedance rate of change signal 855, a RV septal wall (S) intracardiac local impedance rate of change signal 865, and a RV apex (RV) intracardiac local impedance rate of change signal 875. In some examples, the cardiac dyssynchrony detector 320 uses a relationship between the three intracardiac local impedance rate of change signals to detect dyssynchrony. In some examples, a temporal relationship is used. The cardiac dyssynchrony detector 320 determines one or more time intervals 870A, 870B between indications of a systolic phase of the three cardiac regions. In some examples, the cardiac dyssynchrony detector 320 uses a time interval between peaks 880A, 880B, and 880C of the signals to detect dyssynchrony. In some examples, the cardiac dyssynchrony detector 320 establishes one or more baselines for the time intervals and detects dyssynchrony when at least one measured time interval changes from at least one baseline time interval by a specified amount. In some examples, the cardiac dyssynchrony detector 320 uses a correlation analysis among the three intracardiac impedance signals to detect dyssynchrony.

According to some examples, the second sensing circuit 315 of FIG. 3 includes an intrinsic heart signal sensor and the second sensor signal includes an intrinsic heart signal representative of electrical cardiac activity. The cardiac dyssynchrony detector 320 detects cardiac dyssynchrony using the relationship of the intracardiac local impedance signal and a feature of the intrinsic heart signal. The intrinsic heart signal includes a heart chamber contraction indication. In certain examples, the heart contraction indication includes a sensed QRS complex indicating depolarization of a first ventricular. The intracardiac local impedance signal also includes an indication of a heart chamber contraction, such as an indication of a systolic phase of a second ventricle. The cardiac dyssynchrony detector 320 detects dyssynchrony when the heart contraction indications differ by a time interval or by a time interval that exceeds an interventricular delay threshold value. In some examples, the cardiac dyssynchrony detector 320 detects dyssynchrony using the intrinsic heart signal and a rate of change of the intracardiac local impedance signal.

In some examples, the second sensing circuit 315 includes an implantable acceleration sensor, such as an accelerometer. The second sensor signal includes an intracardiac acceleration signal indicative of cardiac wall motion. In certain examples, the accelerometer is included on a cardiac lead and is placed against a myocardial wall to sense cardiac wall motion. The cardiac dyssynchrony detector 320 detects dyssynchrony when a heart contraction indication on the accelerometer signal differs from a heart chamber contraction indication on the intracardiac local impedance signal by a time interval or by a time interval that exceeds an interventricular delay threshold value. In some examples, the cardiac dyssynchrony detector 320 detects dyssynchrony using the accelerometer signal and a rate of change of the intracardiac local impedance signal.

Figure 9:
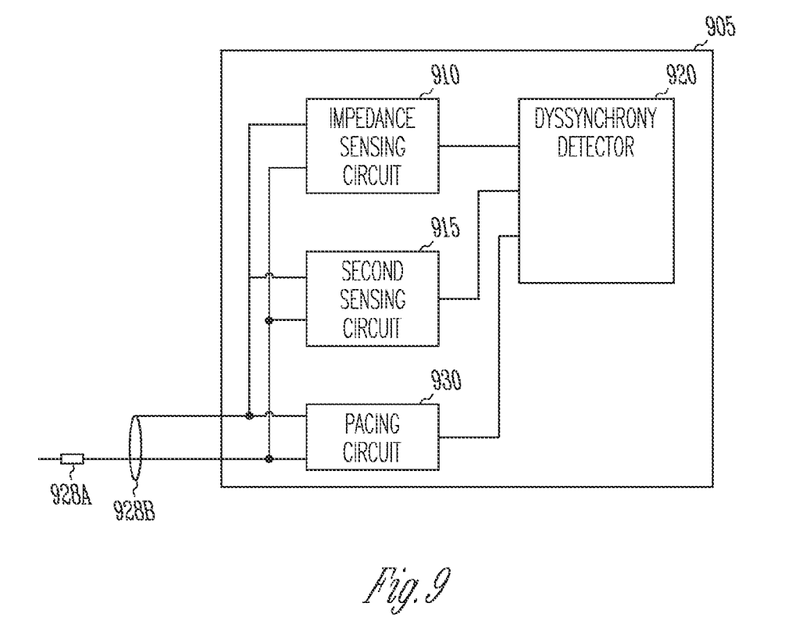
FIG. 9 shows a block diagram of portions of another example of a device for monitoring cardiac impedance of a subject.

FIG. 9 shows a block diagram of portions of another example of a device 905 for monitoring cardiac impedance of a subject. The device 905 includes an impedance sensing circuit 910, a second sensing circuit 915 to produce a second sensor signal indicative of cardiovascular activity, and an impedance-based cardiac dyssynchrony detector 920. The device 905 also includes at least one electrode, such as tip electrode 928A or ring electrode 928B, configured for providing electrical stimulation energy to a ventricle. The device 905 further includes a pacing circuit 930 coupled to the electrode. The pacing circuit 930 changes the timing of delivery of electrical stimulation energy to the ventricle according to local impedance indicated cardiac dyssynchrony. For example, returning to FIG. 5, the pacing circuit 930 may pace the LV, or alter the pacing, to reduce or minimize the time interval 570 between contractions of the RV and the LV in order to correct the dyssynchrony.

In some examples, the device includes at least a first electrode to provide electrical stimulation energy to a first heart chamber and at least a second electrode to provide electrical stimulation energy to a second heart chamber that is different from the first heart chamber. The pacing circuit 930 changes the relative timing of delivery of electrical stimulation energy to the first and second heart chamber according to local impedance indicated cardiac dyssynchrony. For example, the pacing circuit 930 may pace both the RV and LV, and change the relative timing of pacing energy delivered to the RV and LV to reduce or minimize the time interval between contractions of the RV and the LV in order to correct the dyssynchrony.

In some examples, the pacing circuit 930 alters an intrachamber pacing electrode selection according to local impedance indicated cardiac dyssynchrony. For example, the pacing circuit 930 may provide electrical stimulation energy between electrode 228A and electrode 228B in FIG. 2. Based on indicated cardiac dyssynchrony, the pacing circuit 930 may instead provide electrical stimulation energy between electrode 228B and 228C.

It is to be understood that the above description is intended to be illustrative, and not restrictive. For example, the above-described embodiments (and/or aspects thereof) may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to comply with 37 C.F.R. §1.72 (b), which requires that it allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment.

What is claimed is:

1. An apparatus comprising:
a first impedance sensing circuit to sense a first intracardiac local impedance signal from an implantable first bipolar pair of impedance sensing electrodes, wherein the first intracardiac local impedance signal is indicative of a cardiac local wall motion of a first cardiac region;
a second sensing circuit configured to produce a second sensor signal indicative of cardiovascular activity, wherein the second sensor signal includes a second intracardiac local impedance signal and is indicative of a cardiac local wall motion of a second cardiac region; and
an impedance-based cardiac dyssynchrony detector configured for detecting cardiac dyssynchrony using a relationship between the first intracardiac local impedance signal and the second sensor signal, wherein the cardiac dyssynchrony detector is configured for detecting cardiac dyssynchrony using a correlation between the first intracardiac local impedance signal and the second intracardiac local impedance signal.

2. The apparatus of claim 1, wherein the second sensing circuit includes a second impedance sensing circuit to sense the second intracardiac local impedance signal from a second bipolar pair of impedance sensing electrodes.

3. The apparatus of claim 2, including a third impedance sensing circuit configured to sense a third intracardiac local impedance signal from a third bipolar electrode pair, wherein the third intracardiac local impedance signal is indicative of a cardiac local wall motion of a third cardiac region,
wherein the first, second, and third bipolar electrode pairs are configured for placement in first, second, and third cardiac regions that include at least a ventricle free wall region and a ventricle septal wall region, and
wherein the cardiac dyssynchrony detector is further configured for detecting cardiac dyssynchrony using the first, second, and third intracardiac local impedance signals.

4. The apparatus of claim 3, wherein at least one of the first, second, and third cardiac regions includes a ventricular apical region.

5. The apparatus of claim 1, including a third sensing circuit, wherein the third sensing circuit includes an intrinsic cardiac signal sensor to produce an intrinsic heart signal representative of electrical cardiac activity, and wherein the cardiac dyssynchrony detector is configured for detecting cardiac dyssynchrony using a relationship of the first intracardiac local impedance signal, the second intracardiac local impedance signal, and a feature of the intrinsic heart signal.

6. The apparatus of claim 1, wherein the cardiac dyssynchrony detector includes:
a baseline module configured for establishing a baseline time interval between a first indication of a heart chamber contraction associated with the intracardiac local impedance signal and a second indication of the heart chamber contraction associated with the second sensor signal; and
wherein the cardiac dyssynchrony detector is configured for detecting cardiac dyssynchrony when a measured time interval between the first and second indications changes from the baseline time interval by a specified amount.

7. The apparatus of claim 1, wherein the cardiac dyssynchrony detector is configured for detecting cardiac dyssynchrony using a rate of change of the intracardiac local impedance signal.

8. The apparatus of claim 7, wherein the second sensing circuit includes a second impedance sensing circuit to sense a second intracardiac local impedance signal from a second bipolar electrode pair, wherein the second sensor signal includes the second intracardiac local impedance signal and is indicative of a cardiac local wall motion of a second cardiac region, and
wherein the cardiac dyssynchrony detector further includes:
a baseline module configured for establishing a baseline time interval between a first indication of a heart chamber contraction associated with a rate of change of the first intracardiac local impedance signal and a second indication of the heart chamber contraction associated with a rate of change of the second intracardiac local impedance signal; and
wherein the cardiac dyssynchrony detector is configured for detecting cardiac dyssynchrony when a measured time interval between the first and second indications changes from the baseline time interval by a specified threshold time interval value.

9. The apparatus of claim 1, wherein a distance between first and second electrodes of the first bipolar electrode pair is in a range of approximately 2 millimeters to 40 millimeters.

10. The apparatus of claim 1, wherein a distance between first and second electrodes of the first bipolar pair of impedance sensing electrodes is within approximately 20 millimeters.

11. The apparatus of claim 1, including:
at least a first electrode configured for providing electrical stimulation energy to a first heart chamber;
at least a second electrode configured for providing electrical stimulation energy to a second heart chamber different from the first heart chamber; and
a pacing circuit coupled to the first and second electrodes, the pacing circuit configured for changing the relative timing of delivery of electrical stimulation energy to the first and second heart chamber according to local impedance indicated cardiac dyssynchrony.

12. The apparatus of claim 1, including:
at least one electrode configured for providing electrical stimulation energy to a ventricle; and
a pacing circuit coupled to the electrode, the pacing circuit configured for changing the timing of delivery of electrical stimulation energy to the ventricle according to local impedance indicated cardiac dyssynchrony.

13. An apparatus comprising:
a first impedance sensing circuit to sense a first intracardiac local impedance signal from an implantable first bipolar pair of impedance sensing electrodes, wherein the first intracardiac local impedance signal is indicative of a cardiac local wall motion of a first cardiac region;
a second sensing circuit configured to produce a second sensor signal indicative of cardiovascular activity, wherein the second sensing circuit includes an implantable accelerometer and the second sensor signal includes an accelerometer signal indicative of cardiac wall motion and
an impedance-based cardiac dyssynchrony detector configured for detecting cardiac dyssynchrony using a relationship between the first intracardiac local impedance signal and the second sensor signal.

14. The apparatus of claim 13, including:
at least one electrode configured for providing electrical stimulation energy to a ventricle; and
a pacing circuit coupled to the electrode, the pacing circuit configured for changing the timing of delivery of electrical stimulation energy to the ventricle according to local impedance indicated cardiac dyssynchrony.

15. The apparatus of claim 13, wherein the cardiac dyssynchrony detector includes:
a baseline module configured for establishing a baseline time interval between a first indication of a heart chamber contraction associated with the intracardiac local impedance signal and a second indication of the heart chamber contraction associated with the second sensor signal; and
wherein the cardiac dyssynchrony detector is configured for detecting cardiac dyssynchrony when a measured time interval between the first and second indications changes from the baseline time interval by a specified amount.

16. An apparatus comprising:
a first impedance sensing circuit to sense a first intracardiac local impedance signal from an implantable first bipolar pair of impedance sensing electrodes, wherein the first intracardiac local impedance signal is indicative of a cardiac local wall motion of a first cardiac region;
a second sensing circuit configured to produce a second sensor signal indicative of cardiovascular activity;
an impedance-based cardiac dyssynchrony detector configured for detecting cardiac dyssynchrony using a relationship between the first intracardiac local impedance signal and the second sensor signal;
at least a first electrode configured for providing electrical stimulation energy to a first heart chamber;
at least a second electrode configured for providing electrical stimulation energy to a second heart chamber different from the first heart chamber; and
a pacing circuit coupled to the first and second electrodes, the pacing circuit configured for altering an intrachamber pacing electrode selection according to local impedance indicated cardiac dyssynchrony.

17. The apparatus of claim 16, wherein the second sensing circuit includes an implantable accelerometer and the second sensor signal includes an accelerometer signal indicative of cardiac wall motion.

18. The apparatus of claim 16, wherein the second sensor signal includes the second intracardiac local impedance signal and is indicative of a cardiac local wall motion of a second cardiac region, wherein the cardiac dyssynchrony detector is configured for detecting cardiac dyssynchrony using a correlation between the first intracardiac local impedance signal and the second intracardiac local impedance signal.

19. A method comprising:
sensing an intracardiac local impedance signal indicative of a cardiac local wall motion using an implantable medical device (IMD);
sensing at least a second sensor signal indicative of cardiovascular activity, wherein sensing the second sensor signal includes sensing a second intracardiac local impedance signal; and
detecting cardiac dyssynchrony using a relationship between the intracardiac local impedance signal and the second sensor signal, wherein detecting cardiac dyssynchrony includes using a correlation between the first local impedance signal and the second local impedance signal.

20. The method of claim 19, wherein detecting cardiac dyssynchrony includes:
establishing a baseline time interval between a first indication of a heart chamber contraction associated with the intracardiac local impedance signal and a second indication of the heart chamber contraction associated with the second sensor signal; and
detecting cardiac dyssynchrony when a measured time interval between the first and second indications changes from the baseline time interval by a specified amount.

21. The method of claim 19,
wherein sensing the intracardiac local impedance signal includes sensing a first local impedance signal indicative of local cardiac wall motion of a first local ventricular region using a first bipolar pair of impedance sensing electrodes; and
wherein sensing the second sensor signal includes sensing a second local impedance signal indicative of cardiac wall motion of a second local ventricular region using a second bipolar pair of impedance sensing electrodes.

22. The method of claim 21, wherein the first local ventricular region includes a local region of the left ventricle free wall and the second local ventricular region includes a local region of the right ventricle septal wall.

23. The method of claim 21, wherein the first local ventricular region includes a local region of the left ventricle free wall and the second local ventricular region includes a local region of the right ventricle free wall.

24. The method of claim 21, wherein the first local ventricular region includes a local region of the left ventricle free wall and the second local ventricular region includes a local region of the right ventricle apex.

25. The method of claim 19, including sensing a third sensor signal, wherein sensing the third sensor signal includes sensing an intrinsic heart signal produced by an intrinsic heart signal sensor, the intrinsic heart signal representative of cardiac activity, and wherein detecting cardiac dyssynchrony includes using a relationship between the intracardiac local impedance signal, the second sensor signal, and the third sensor signal.

26. The method of claim 19, wherein detecting cardiac dyssynchrony includes using a rate of change of the intracardiac local impedance signal.

27. The method of claim 26,
wherein sensing the intracardiac local impedance signal includes sensing a first local impedance signal indicative of local cardiac wall motion of a first local ventricular region;
wherein sensing the second sensor signal includes sensing at least a second local impedance signal indicative of cardiac wall motion of at least a second local ventricular region; and
wherein detecting cardiac dyssynchrony includes:
establishing a baseline time interval between a first indication of a heart chamber contraction associated with the rate of change of the first intracardiac local impedance signal and a second indication of the heart chamber contraction associated with the rate of change of the second sensor signal; and
detecting cardiac dyssynchrony when a time interval between the first and second indications changes from the baseline time interval by a specified amount.

28. The method of claim 27,
wherein sensing the first local impedance signal includes sensing the first local impedance signal from a local region of a left ventricle free wall; and
wherein sensing at least a second local impedance signal includes sensing the second local impedance signal from a local region of at least one of a right ventricle septal wall and a right ventricle free wall.

29. The method of claim 28, wherein sensing at least a second local impedance signal includes:
sensing the second local impedance signal from a local region of a right ventricle septal wall;
sensing a third local impedance signal from a local region of a right ventricle free wall; and
wherein detecting cardiac dyssynchrony includes:
establishing one or more baseline time intervals between the first indication, the second indication, and a third indication of the heart chamber contraction associated with the rate of change of the third sensor signal; and
detecting cardiac dyssynchrony when at least one measured time interval among the first, second, and third indications changes from the baseline time interval by a specified amount.

30. The method of claim 19, further including changing a relative timing of delivery of electrical stimulation energy to a first heart chamber and a second heart chamber according to local impedance indicated cardiac dyssynchrony.

31. The method of claim 19, further including changing the timing of delivery of electrical stimulation energy to a ventricle according to local impedance indicated cardiac dyssynchrony.

32. A method comprising:
sensing an intracardiac local impedance signal indicative of a cardiac local wall motion using an implantable medical device (IMD);
sensing at least a second sensor signal indicative of cardiovascular activity, wherein sensing the second sensor signal includes sensing an intracardiac acceleration signal indicative of cardiac wall motion, the intracardiac acceleration signal produced by an implantable acceleration sensor; and
detecting cardiac dyssynchrony using a relationship between the intracardiac local impedance signal and the second sensor signal.

33. The method of claim 32, further including changing a relative timing of delivery of electrical stimulation energy to a first heart chamber and a second heart chamber according to local impedance indicated cardiac dyssynchrony.

34. The method of claim 32, wherein detecting cardiac dyssynchrony includes:
establishing a baseline time interval between a first indication of a heart chamber contraction associated with the intracardiac local impedance signal and a second indication of the heart chamber contraction associated with the second sensor signal; and detecting cardiac dyssynchrony when a measured time interval between the first and second indications changes from the baseline time interval by a specified amount.

35. A method comprising:

sensing an intracardiac local impedance signal indicative of a cardiac local wall motion using an implantable medical device (IMD);

sensing at least a second sensor signal indicative of cardiovascular activity;

detecting cardiac dyssynchrony using a relationship between the intracardiac local impedance signal and the second sensor signal; and altering an intrachamber pacing electrode selection according to local impedance indicated cardiac dyssynchrony.

36. The method of claim 35, wherein sensing the second sensor signal includes sensing an intrinsic heart signal produced by an intrinsic heart signal sensor, the intrinsic heart signal representative of cardiac activity.

37. The method of claim 35, wherein sensing the intracardiac local impedance signal includes sensing a first local impedance signal indicative of local cardiac wall motion of a first local ventricular region, and wherein sensing the second sensor signal includes sensing a second local impedance signal indicative of cardiac wall motion of a second local ventricular region.

* * * * *